United States Patent [19]

Smolen

[11] 4,279,860
[45] Jul. 21, 1981

[54] MULTIPLE INJECTOR FLOW THROUGH DISSOLUTION CELL FOR DISSOLUTION TESTING APPARATUS

[76] Inventor: Victor F. Smolen, Anchorage Lodge, Rouses Point, N.Y. 12979

[21] Appl. No.: 162,780

[22] Filed: Jun. 25, 1980

[51] Int. Cl.³ .............................................. G01N 21/13
[52] U.S. Cl. ..................................... 422/63; 422/100
[58] Field of Search ................................... 422/63–65, 422/68, 69, 99, 120, 269, 270, 100

[56] References Cited

U.S. PATENT DOCUMENTS

| | | | |
|---|---|---|---|
| 3,508,879 | 4/1970 | Findl et al. | 422/65 X |
| 3,684,452 | 8/1972 | Bessman | 422/64 |
| 3,787,291 | 1/1974 | Deuringer et al. | 422/68 X |
| 4,019,861 | 4/1977 | Dahms | 422/68 X |

*Primary Examiner*—William A. Cuchlinski, Jr.

*Attorney, Agent, or Firm*—James F. Cottone

[57] ABSTRACT

A dissolution cell for use in automatic dissolution testing apparatus is specially configured to accommodate the iterative insertion of product specimens into the dissolution mechanism flow stream, and to perform the specimen insertion into a stabilized flow stream with minimal insertion disturbance. A basic multiple-injection embodiment utilizes a linear configuration to selectively insert two specimens into the flow stream, and a circular multiple-injection embodiment teaches the selective insertion of a plurality of specimens into the stream in a manner amenable to a programmable sequence. Both embodiments use air evacuation of the specimen flow chamber prior to its insertion into the instrumented flow stream, and both allow a high degree of fidelity in the dissolution measurements performed. The improved cell is especially useful for testing rapidly dissolving industrial products or drug dosage forms.

9 Claims, 7 Drawing Figures

MULTIPLE INJECTOR FLOW THROUGH DISSOLUTION CELL FOR DISSOLUTION TESTING APPARATUS

BACKGROUND OF THE INVENTION

1. Field of the Invention

The present invention relates generally to the field of automatic dissolution testing of products whose solubility and dissolution rate properties affect product performance, and more specifically to an improved dissolution cell specially configured to accommodate the rapid and iterative insertion of product specimens into the dissolution medium of the testing system.

The dissolution cell is configured with a plurality of flow channels, each of which may contain a product specimen, and is operable to insert a selected flow channel/product specimen into the dissolution measurement chamber with a minimal impact on the initial conditions established within the testing system.

2. Description of the Prior Art

Dissolution testing of components of industrial products whose solubility and dissolution rate properties affect product performance can be used as a screening and quality control tool. The solubility properties of solid materials can depend on polymorphic crystalline form, crystal habit, crystal shape, particle size and particle size distribution, and state of solvation. A simple and rapidly performed dissolution test can substitute for the determination of these physical properties by more time consuming and expensive methods such as x-ray crystallography, differential thermal analysis, microscopy, etc. The materials are instead determined as to whether they conform to a dissolution rate standard under specified conditions and in relation to a known reference sample of the same material characterized by the above physical properties and possessing the derived dissolution rate and solubility performance.

The broad technique of determining dissolution rate properties is especially of interest in the testing of drug products where the therapeutic performance of drugs is closely related to the drug dissolution properties. Seemingly minor changes in drug product formulation, as well as the inadvertent variation in materials and manufacture that can occur between batches of the same product formulation, can influence the therapeutic performance of drugs. In vivo bioavailability testing of drug products in humans provides the most reliable means of ensuring bioequivalence. However, it is impractical to perform the extensive and expensive human testing that would be routinely required. Large numbers of human subjects would be placed at risk if such studies were conducted. Bioavailability testing in which humans are used as test subjects can be minimized by the development and implementation of in vitro dissolution standards that reflect in vivo drug-product performance. In vitro bioequivalence requirements have been established for some drugs such as digoxin. From among the various chemical and physical tests that can be performed on drug solids in vitro for correlating or predicting a drug product's in vivo bioavailability behavior, dissolution testing is the most sensitive and reliable. The correlative relationships most commonly reported between in vitro dissolution and in vivo bioavailability are of the single-point type: the percentage of the drug dissolved in a given time (or the time it takes to dissolve a given percentage of the drug in vitro) and some univariate characteristic of the drug product's in vivo response versus time profile (such as the peak blood level, the time required to reach the peak or 50% of the peak, or the area under the blood-level curves) are correlated. The selection of in vitro dissolution and in vivo bioavailability parameters for such single-point correlations is frequently arbitrary, and the results can be misleading. Obviously, it would be preferable to predict the entire average blood level, urinary recovery rate, pharmacological-response-time, or drug absorption rate vs. time profile that would be elicited by a drug product in a panel of human subjects rather than merely to correlate univariate characteristics of the dissolution profile with an in vivo bioavailability parameter. In all cases, however, the fidelity of the in vitro dissolution results in correlating and in predicting in vivo drug-product bioavailability depends upon the dissolution-test process variables, such as the dissolution-medium composition, the solubility volume of the medium (sink conditions that determine the extent to which the medium becomes saturated with the drug), and the agitation rates (stirring or flow rates). An improper choice of these process variables (e.g., an excessively high rate of agitation) can mask significant bioavailability differences among drug products. On the other hand, the dissolution test can be overly sensitive in detecting differences that are negligible in vivo. In the former case, using such improper dissolution-test parameters would result in the marketing of therapeutically ineffective drug products. In the latter case, the result would be the discarding of drug products that are entirely satisfactory in terms of in vivo performance. Serious economic losses could result from the use of an overly sensitive in vitro dissolution test for lot-to-lot reproducibility testing of drug products. Therefore, whether the dissolution test is being used as a quality control tool, as an in vivo bioequivalency requirement for multisource generic drug products, or as a substitute for human bioavailability testing during the development of new drug-product formulations, it is imperative that the dissolution test provide predictive results that are biologically relevant.

A detailed description of an automatic dissolution testing system which employs an online microprocessor to continually optimize a set of process variables may be found in a copending application by the same inventor as the present application entitled, "Method and Apparatus for Automatic Dissolution Testing of Products". That application was filed on Apr. 17, 1980 and bears the Ser. No. 141,093.

A significant and troublesome problem inherent in automatic dissolution testing is encountered during the testing of products which have very rapid dissolution rates. This is especially true when the dissolution times of the product specimens involved are short compared to the time constants of the automatic testing system. Thus, the present improved dissolution cell which permits new and useful operating modes is directed to overcoming these problems, and greatly enhances the usefulness of the automatic dissolution testing art.

SUMMARY OF THE INVENTION

It is therefore a primary object of the present invention to provide an improved dissolution cell for use with automatic dissolution testing apparatus.

Another object of the present invention is to provide an improved multiple-injection dissolution cell for rapidly and/or iteratively inserting a product specimen into a dissolution testing system.

Another object of the present invention is to provide an improved dissolution cell having a plurality of flow channels each configured to contain a product specimen and to be selectively inserted into a dissolution flow medium under control of an operator, or an automatic sequencing means.

Another object of the present invention is to provide an improved dissolution cell having a plurality of flow channels each configured to contain a product specimen, and further having means for evacuating the air out of a flow channel prior to its being inserted into a dissolution chamber in which a dissolution medium is flowing.

A still further object of the present invention is to provide an improved dissolution cell having a plurality of flow channels and means for evacuating air out of selected channels such that a product specimen within a particular flow channel can be inserted into a dissolution chamber so as to minimally impact on the preexisting flow of dissolution medium within the chamber.

A further object of the present invention is to provide a multiple-injection dissolution cell wherein a plurality of selectable flow channels may be configured either as a linear array or a circular array to facilitate the rapid and/or automatic alignment of each flow channel successively with the dissolution chamber of a testing system.

BRIEF DESCRIPTION OF THE DRAWINGS

Additional objects and advantages of the invention will become apparent to those skilled in the art as the description proceeds with reference to the accompanying drawings wherein.

DETAILED DESCRIPTION OF THE PREFERRED EMBODIMENTS

Figure 1:
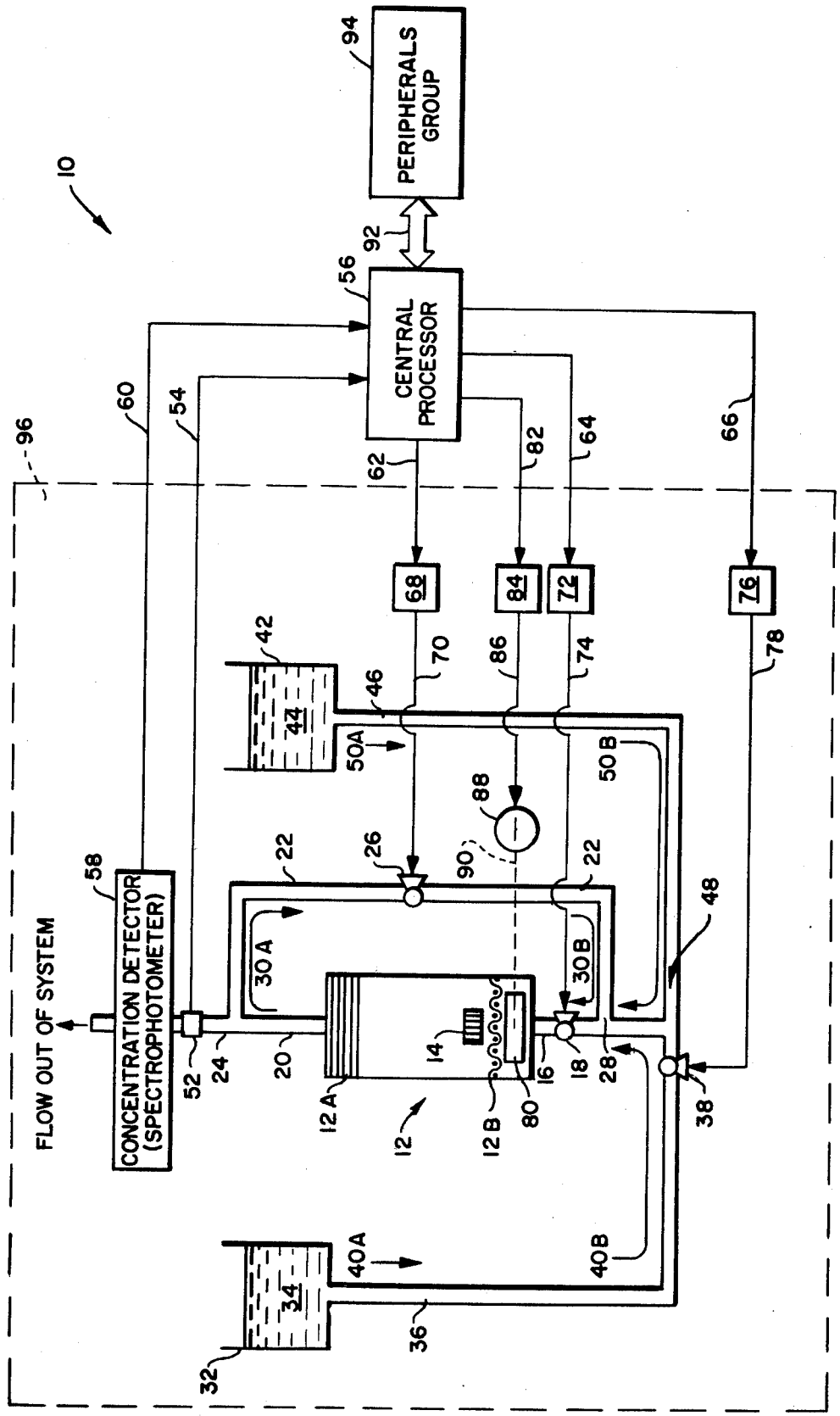
FIG. 1 is an overall block diagram of an automatic dissolution testing system utilizing the improved, multiple-injection dissolution cell of the present invention.

Referring now to FIG. 1, there is shown a block diagram of an automatic flow-through dissolution testing system in which the multiple injector dissolution cell of the present invention would find its primary application. For simplicity of exposition the various elements are not shown to scale, and the embodiment shown is a basic one. The descriptions throughout this specification are expressed in terms of the testing of a pharmaceutical drug dosage form, and the language is accordingly specific to this usage. Of course, the embodiments disclosed are illustrative and could readily be adapted for use with agricultural products, or with controlled release components of industrial products generally. The overall system 10 is shown as comprised of a basic dissolution cell 12 in which is positioned a specimen of the drug product 14 undergoing evaluation. The cell 12 has a filter membrane 12A and filter screen 12B, and is provided with a flow of various dissolution liquid via a cell input line 16 under the influence of a primary pump 18. Output from the dissolution cell 12 is carried by a cell output line 20 and is routed first via the upper portion of a recirculation line 22, and thereafter via a system output line 24. Within the recirculation line 22 is a recirculation pump 26 which propels the liquid therein into the lower portion of the recirculation line 22, and thereafter into a feeder line 28, which serves as an input to the primary pump 18. The two arrows 30A and 30B show the direction of flow in the recirculation line 22 under the influence of the recirculating pump 26.

A first reservoir 32 is used to contain a supply of a first dissolution medium 34, which is fed via a line 36 to the dissolution cell 12. The first dissolution medium 34, hereinafter alternately called the acid media, is fed to the feeder line 28 under the influence of a pump 38. The flow direction of the acid media 34 is shown by the flow arrows 40A and 40B. A second reservoir 42 is used to contain a supply of a second dissolution medium 44, hereinafter alternately called the alkaline medium 44. The alkaline medium 44 is fed via a line 46 and a check valve 48 to the feeder line 28, and subsequently through the primary pump 28 to the dissolution cell 12. The flow direction of the alkaline media 44 is shown by the flow arrows 50A and 50B. As will be discussed in detail below, the flow path 40B of the acid media 34 is due to the presence of the check valve 48, and the flow path 50B on the alkaline medium 44 is due to the dynamics of the action of the two pumps 38 and 18.

The system output line 24 serves to conduct the flow of the processed media containing the desired concentration of the dissolved drug product out of the system, and further supports two key system measurements. A flow measurement device 52, serially positioned in the output line 24, provides a quantitative measurement of a liquid flow rate via a group of lines 54 to a central processor 56. (Alternatively, this flow rate may be obtained electronically as the difference in control signals to the primary pump 18 and the recycle pump 26.) A spectrophotometer 58, also serially positioned in the output line 24, provides a periodic (or continuous) measurement of the drug concentration in the output flow, and routes this measurement via a group of lines 60 to the central processor 56. Pumps 18, 26 and 38 are of the positive displacement peristaltic type and are capable of producing precisely controlled flow rates in the range of 0.2 to 140 ml per minute when properly controlled. The central processor 56 provides this control via signals on three groups of lines 62, 64 and 66 which modulate the excitation to the pumps as follows. Control signals on the line 62 are applied to a pump speed modulator 68, which in turn controls the excitation of the pump 26 via the lines 70; control signals on the lines 64 are applied to a pump speed modulator 72, which in turn controls the excitation of the pump 18 via the lines 74; the control signals on the line 68 are applied to a pump speed modulator 76, which in turn controls the excitation to the pump 38 via the lines 78. In addition to the above three control signals, the central processor 56 further provides control signals to an agitation means comprised of a stirring paddle 80 located within the dissolution cell 12 and positioned below the filter screen 12B. These control signals are provided on a group of lines 82 to an interface device 84. An output from the interface device 84 is applied via lines 86 to an agitation motor 88, which in turn activates the stirring paddle 80 via the mechanical linkage shown as dashed lines 90. A group of control and data lines 92 interconnect the central processor 56 with a number of supporting units shown as a peripherals group 94. Included within this group 94 would be a data recorder 94A (analog and/or digital), an output printer 94B, and input keyboard 94C, and other well known and conventional devices. An overall measurement block 96 identifies those elements considered to be measurement apparatus, as compared to the remaining elements—56 and 94—which may be considered to be the signal processing and control portions of the system. In use, the system of FIG. 1 carries out the dissolution testing under control of the central processor 56 using operating techniques and modes which do not form an intrinsic part of the present invention.

By way of a very brief overview, the system shown is operable in two modes, the first being a simulative (or closed loop mode); and the second being a predictive (or open loop mode). In these modes, control (proportional, differential and integral) is exercised over one or more of the process variables determined by: (1) the composition; (2) the recycle flow of the dissolution medium; (3) the total flow rate of the dissolution medium; and the rate of agitation within the dissolution cell.

Figure 2:
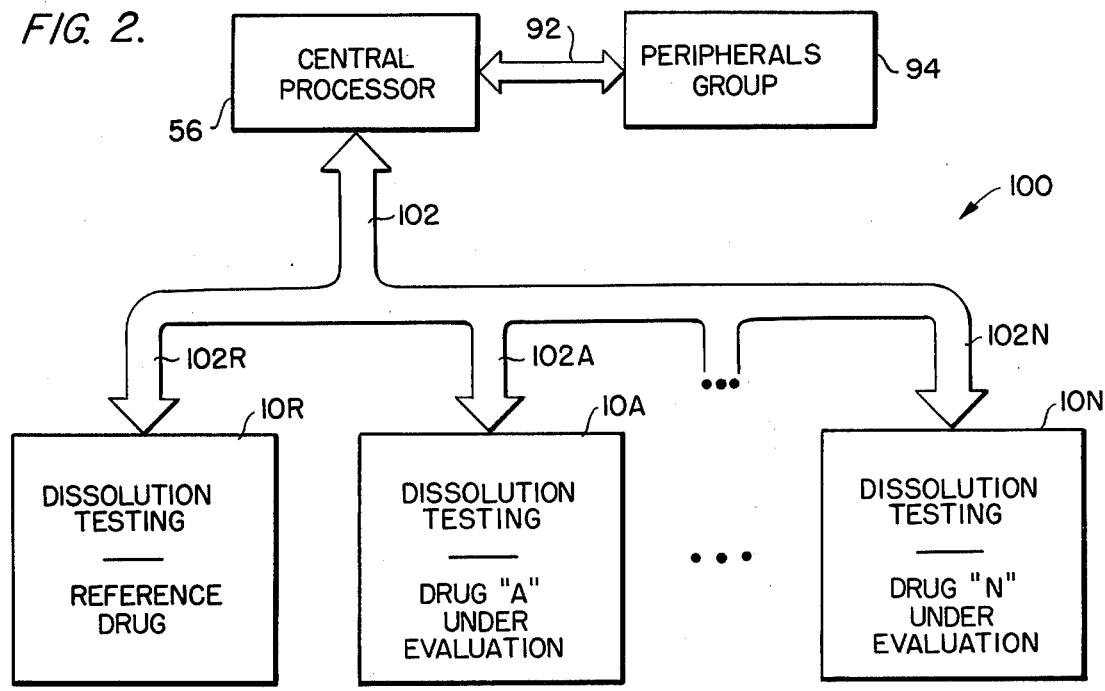
FIG. 2 is an overall block diagram of a dissolution testing system showing operation in an Internal Standard mode wherein multiple and/or iterative product specimens injections are particularly useful.

Referring now to FIG. 2, there is shown a block diagram of an alternate embodiment of the automatic flow-through dissolution testing system wherein a rotary configuration of the multiple injector dissolution cell would be highly useful. The embodiment shown is particularly advantageous in the testing of a number of drug dosage forms simultaneously—by comparison to a reference drug dosage form—and may be used for simultaneously testing large batches of a single drug dosage form, or of simultaneously evaluating a number of different drug dosage forms. The apparatus is basically a parallel arrangement of a plurality of single flow-through dissolution systems as shown in FIG. 1, using a single central processor/peripheral for control. The Internal Standard system 100 is shown as comprised of the elements of the embodiment of FIG. 1, in the form of a central processor 56 interconnected with a peripherals groups 94 via a group of lines 92. A trunk of input/output lines 102 from the central processor 56 are routed to a reference dissolution testing subsystem 10R, via a group of input/output lines 102R; and to a first unknown dissolution testing subsystem 10A via a group of output lines 102A; and further to an "Nth" unknown dissolution testing subsystem 10N via a group of output lines 102N. The number of independent dissolution subsystems may be fairly—a dozen, or more—being limited by purely perfunctory considerations such as cost and convenience in usage. With continued reference to FIG. 2 and occasional reference to FIG. 1, the subsystems 10R, 10A, 10N (of FIG. 2) may be identical to the measurement block 96 (of FIG. 1). The subsystem 10R, in combination with the central processor 56, the peripherals group 94 and the interconnecting lines 92, 102 and 102R constitute a dissolution testing system identical to that of FIG. 1, operating in the closed loop mode of operation as previously described. The subsystems 10A–10N function in the open loop mode as previously described. The primary operating difference is that the N subsystems containing an unknown drug dosage form and operating open loop are controlled simultaneously by the identical control signals being generated by the control processor 56 responsive to the output measurements made on the reference dissolution cell, as compared to the reference drug in vivo dissolution profile. Thus, the in vivo dissolution profile being outputted by the recorder 94A as a time series of known data, in combination with a time series of control signal values produced by the central processor 56 serves as an Internal Standard in the sense that the predictive profiles are produced in the open loop mode by signals which are simultaneously being produced by closed loop mode of operation using a reference drug and data as the basis. A cursory review of the operation of the basic embodiment of FIG. 1, as compared with that of FIG. 2, will reconfirm that only comparatively minor differences in operation of the subsystems are involved. For example, the subsystems 10A–10N have no need to perform the measurement of flow rate and drug concentration in their output lines. Only the subsystem 10R requires that information. In the interest of the uniformity of apparatus, and as a means of providing additional versatility to the Internal Standard system 100, any or all of the subsystems 10A–10N may include the components required to measure these output parameters and provide related signals to the central processor 56. In this latter case, the central processor 56 is merely instructed to ignore the specific output data produced by those particular subsystems which are to be operated open loop.

Summarizing, the Internal Standard embodiment of FIG. 2 includes the signal processing elements (the central processor 56 and peripherals group 94) of FIG. 1, along with a plurality of the measuring blocks 96 of FIG. 1. Of the number of measuring blocks, one (subsystem 10R) serves as a reference subsystem and operates in a closed loop mode with the signal processing elements, while the remainder (subsystems 10A to 10N) are controlled by the signal processing elements in the open loop mode. Thus, the plurality of subsystems 10A–10N each produce a predictive dissolution profile of a separate drug dosage form while all are referenced to a single reference drug dosage form.

Figure 3A:
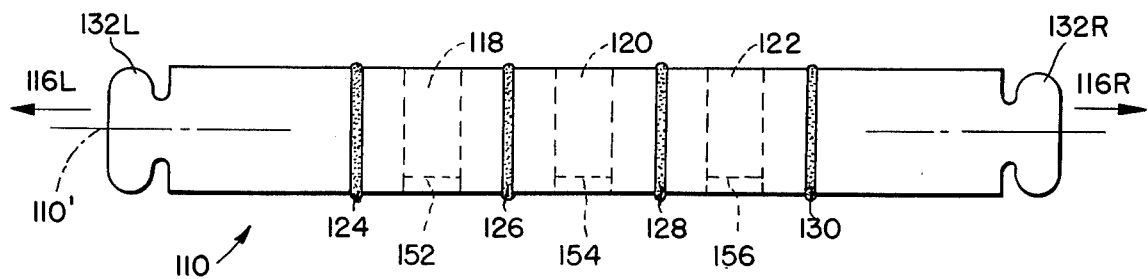
FIGS. 3A-3C show a preferred embodiment of the multiple-injection dissolution cell, in a linear configuration.
Figure 3B:
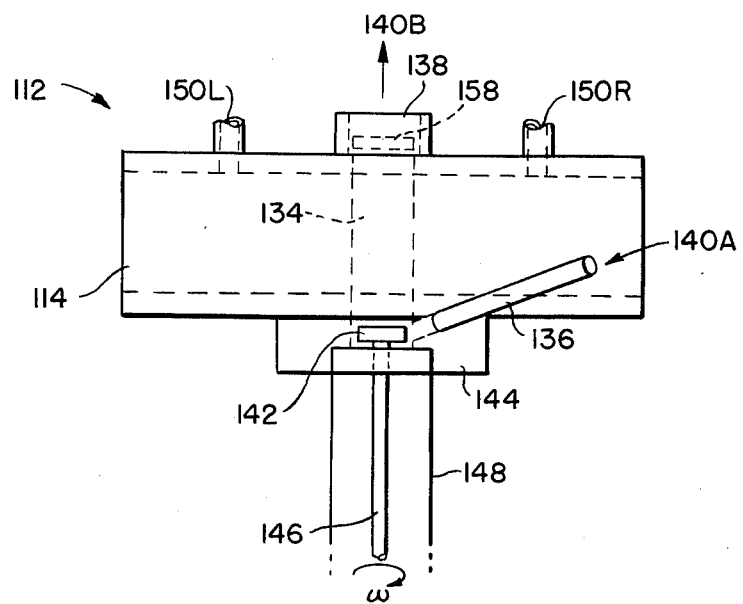
Figure 3C:
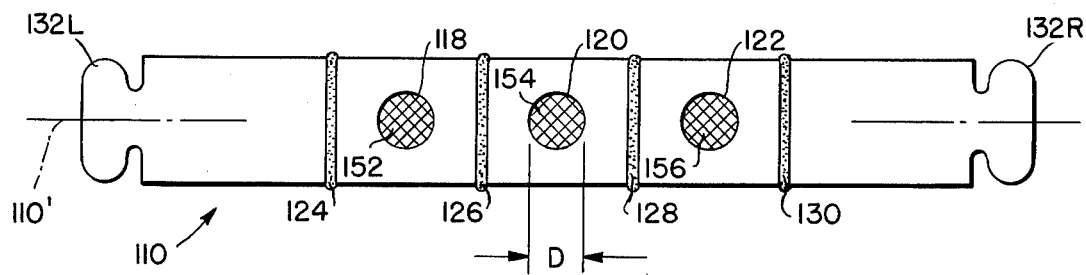

Referring now to FIGS. 3A–3C, there is shown a schematic view of an improved double-injector flow through dissolution cell according to the present invention. FIG. 3A shows an insert member 110 which mates with a corresponding body member 112 of FIG. 3B. The insert 110 has a longitudinal axis 110' and is shaped in elongated cylindrical form so as to fit into a cylindrical aperture 114 formed into the body 112. When so inserted, the insert 110 may be moved within the body 112, piston-cylinder-like to the left and right (along the longitudinal axis 110') as depicted by the arrows 116L and 116R. The insert 110 has three cylindrical flow channels 118, 120 and 122 formed transversely to its longitudinal axis 110', each of which is flanked by a pair of O-rings which provide seals for their included flow channels. Brief reference to FIG. 3C, a top view of the insert 110, shows the flow channels 118, 120 and 122, each having a diameter D, to be regularly aligned along the axis 110', and having their axes in a single vertical plane. The O-rings are positioned in shallow groves (not shown) as is well known. O-rings 124 and 126 flank the flow channel 118, O-rings 126 and 128 flank the flow channel 120, and O-rings 128 and 130 flank the flow channel 122. End knobs 132L and 132R are formed into the extremities of the insert 110 to facilitate left-right movement as described below.

The body 112 has a second cylindrical aperture 134 centrally disposed therein which is oriented transversely to the larger aperture 114. The aperture 134 constitutes the dissolution chamber portion of the flow through dissolution cell, and it has a diameter D equal to that of the flow channels 118, 120 and 122 with which it cooperates. The dissolution chamber 134 has an inlet port located at its lower end which is supplied via an inlet conduit 136, and an outlet port 138 located at its upper end. Flow arrows 140A and 140B indicate the direction of flow through the chamber 134. A stirring paddle 142 is located in the lower end of the chamber 134, or more precisely in an extension of the dissolution chamber 134 which is formed into a joining block 144. The paddle 142 is driven by a shaft 146 at a controllable speed and direction indicated by the rotary motion arrow $\omega$. The shaft 146 is retained by a housing block 148, including appropriate retaining and sealing means (not shown); and is further driven at the controllable rates by an electronically controlled motor (not shown) under the control of the system of FIG. 1. A pair of air evacuation ports 150L and 150R are formed into the body 112 such that their central axes, along with the axes of the dissolution chamber 134, lie in a single vertical plane.

Each of the flow channels 118, 120 and 122 have positioned at their lower extremities a mesh screen which serves to support the solid substances which are to be dissolved. The screens 152, 154 and 156 are of selected mesh sizes, and are positioned in the flow channels 118, 120 and 122, respectively. A filter element 158 is positioned at the upper extremity of the chamber 134, within the outlet port 138 region.

Consider now the dissolution cell as a whole, that is with the insert 110 fitted into the body 112 such that one of the flow channels 118, 120 and 122 is aligned with the dissolution chamber 134. In operation, a specimen of the product whose dissolution characteristics are to be tested is positioned—as described below—in the appropriate flow channel (118 or 122) and the dissolution media is caused to flow from the inlet conduit 136 in the direction of the flow arrows 140A and 140B at a flow rate controlled by an electronically controlled pump (not shown). Agitation of the dissolution media within the dissolution chamber 134 is accomplished at a controlled rate by the action of the paddle 142, thereby producing a homogeneous mixture of the dissolved specimen and the dissolution media.

In the process of testing a number of particular products, or during the dissolution testing of a single product, it is often necessary to establish a particular set of flow conditions before introducing a specimen into the dissolution medium flow stream. Several factors combine to make this sequence valuable. For example, in the computer-controlled systems of FIGS. 1 and 2, it may take several system time constants (several seconds, or even several minutes) to properly initialize the system; to achieve the desired steady state flow condition of the right mix (pH) of dissolution media; and at the desired flow rates, both total flow rate and recycle flow rate. The time constants involved may be constrained to be long relative to the product being tested which may have very rapid dissolution characteristics. Thus, in the conventional testing approaches, the fidelity of dissolution characteristics may be seriously compromised by the initial transits inherent in both the testing apparatus as well as in the product itself. Additionally, during the simulative mode of operation of a computer-controlled dissolution testing system, it may be necessary to conduct a testing sequence a number of times—distinct runs, iteratively done—in order to progressively tune and optimize the control parameters of the control loop. In this case, the ability to iteratively and quickly insert product specimens into the dissolution chamber without inadvertently changing any of the other system variables also contributes to the efficacy of the optimizing process.

Taking first the situation where a rapidly dissolving product is to be tested, the dissolution testing system is first initialized with, for example, the flow chamber 120 aligned with the dissolution chamber 134. The flow chamber 120 would be free of any product specimen and either or both of the flow chambers 118 and 122 would contain a specimen of the rapidly dissolving product to be tested positioned on the corresponding screens 52 and 56. Assume in this case that the flow chamber 122 alone contains a specimen. The dissolution testing system cycle is initiated, and following the initial transients, the desired pH, flow rate, agitation rate, (and other parameters), as determined from previous in vivo or in vitro tests are eventually established. During this process step, the air is evacuated from the chamber 122 (and chamber 118) via the evacuation port 150R (and port 150L). This is done to prevent the introduction of unwanted air into the flow streams 140A/140B, which may result in interference with the dissolution process. After this is accomplished, the insert 110 is moved to the left thereby aligning flow channel 122 with the dissolution chamber 134 and inserting the product specimen into the dissolution media stream. Obviously, this may be done with a minimum of disruption to the remainder of the apparatus. Clearly, a concentration detector positioned somewhere beyond the outlet port 138 would immediately begin reflecting the dissolution characteristics of the specimen and the resulting measurements would be referenced to a pre-existing transient-free set of baseline measurements. The data thus obtained on the rapidly dissolving product would be a faithful reflection of the dissolution characteristics of the rapidly dissolving product uncontaminated by apparatus initial conditions and the presence of air in the flow stream.

By having a number of flow chambers available—in the preferred embodiment described above, there are three—it is further possible to facilitate the performance of iterative tests of a particular product. This would be done by placing a few (2) identical product specimens on the screens 152 and 156 of flow chambers 118 and 122, and keeping flow channel 120 clear as before. After the desired pH, flow rates, agitation rate, and so forth have been established, as determined by previously obtained reference data, or by predecessor testing cycles, the insert 110 would be moved to introduce the first of the two identical specimens into the dissolution chamber 134. Thereafter, the optimizing process of the control system operating in the simulative mode may be initiated to obtain the best simulation possible. This is done, as previously described, by varying the four key process control variables such that the dissolution profile being generated by the testing system is forced to closely correspond to the previously obtained reference dissolution profile. Should it be necessary to conduct additional dissolution tests on the same product specimen to successively approach the most optimum set of four key control variables and/or to further tune the electronic process controller, the presently available (best current estimate) time sequence of key control variables would be retained, and a second dissolution testing cycle would be initiated. The second cycle is initiated as before, and the second identical product specimen would be inserted into the dissolution chamber 134 by appropriate movement of the insert 110. Using the key control variables optimizing technique previously described, a second set—and invariably a better fit set—of key control variables is then obtained. This iterative process could be repeated as often as necessary until an acceptably good fit between simulative measurements and known reference data is found.

Thus, it is seen that the double-injector embodiment of a flow through dissolution cell naturally compliments the automated dissolution testing processes as outlined in the descriptions of FIGS. 1 and 2, and introduces significantly distinct and highly useful operating modes into the basic systems. Of course, embodiments where the number of flow channels is greater than three are also feasible. In that case, the multiple-injection embodiment would be used operationally the same as described above, with the exception that an additional number of iterations are made possible for the various testing cycles.

Figure 4A:
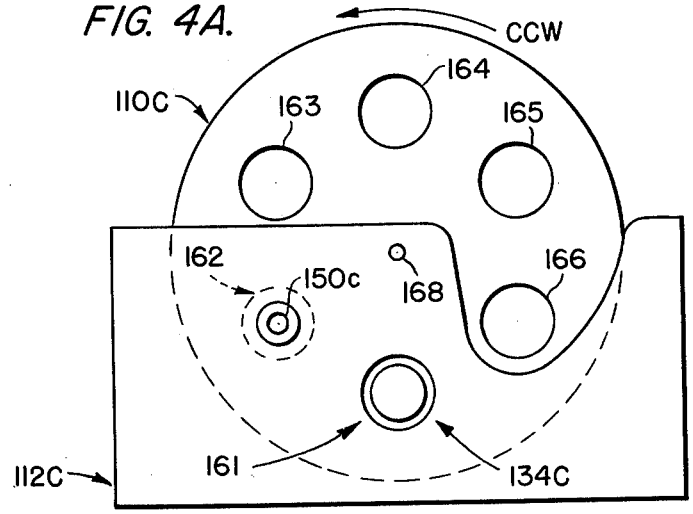
FIGS. 4A and 4B show an alternate embodiment of the multiple-injection dissolution cell in a rotary configuration.
Figure 4B:
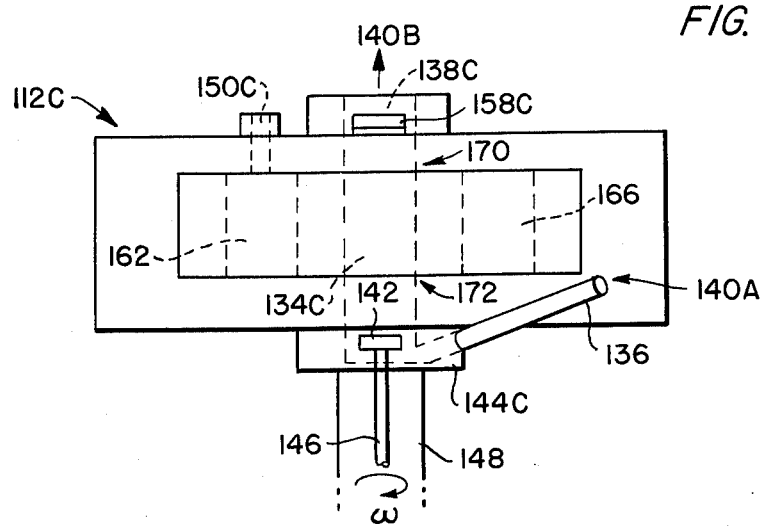

Referring now to FIGS. 4A and 4B, a top view and side view, respectively, of a circular, multiple-injection embodiment is shown. Basically, the circular embodiment shown is fully analogous to the linear configuration of FIGS. 3A–3C, and is structured so as to function substantially the same. Elements of the circular embodiment which are identical to the linear embodimemt are identically numbered, and elements which are closely analogous in structure or function carry the corresponding member with a "C" suffix. Thus, for example, the body member 112 of FIGS. 3A–3C becomes the body member 112C of FIGS. 4A and 4B.

As shown in the top view of FIG. 4A, the circular embodiment provides, illustratively, six flow channels 161–166 (analogous to the flow channels 118, 120 and 122), uniformly positioned within an insert member 110C which is pivoted to rotate about a pivot axis 168. The flow channel 161 is shown as being aligned with the dissolution chamber 134C positioned within the body member 112C. Under counterclockwise (CCW) rotation of the insert member 110C, the flow chamber 162 would next be aligned with the dissolution chamber 134C, and is thus prepositioned so as to be aligned with the air evacuation port 150C. For clarity of illustration, the screens and filter member (elements 152, 158, etc. of FIG. 3A), and other elements, have been omitted from FIG. 4A, but are of course, also employed in this circular embodiment. The side view of FIG. 4B shows the filter element 158C positioned in the outlet port 138C, and regions 170 and 172 which contain ring sealing means (not shown) at the upper and lower extremities, respectively, of the dissolution chamber 134C.

The circular embodiment may function similarly to the linear embodiment with the simple benefit of providing a larger number of flow chambers; or may advantageously be used to support an additional operating mode for the automatic dissolution testing apparatus of FIG. 1. The circular arrangement is particularly well suited for automated operation of the apparatus without the intervention of a human operator to replace specimens in the flow channels. Thus, the flow channels can be preloaded with specimens placed on the screens and the insert member 110C may be motor driven to position each successive specimen, following evacuation of air, into the flow stream in a programmed automatic sequence.

Although the invention has been described in terms of selected preferred embodiments (a linear and a circular configuration), the invention should not be deemed limited thereto, since other embodimens and modifications will readily occur to one skilled in the art. It is therefore to be understood that the appended claims are intended to cover all such modifications as fall within the true spirit and scope of the invention.

What is claimed is:

1. A multiple-injector dissolution cell comprising:
   (a) a body member having a central aperture, and a dissolution chamber positioned between an input port region and an output port region;
   (b) a moveable insert member having a plurality of flow channels and adapted for an air tight fit within said aperture;
   (c) means for selectively moving said moveable insert member within said aperture to align one of said flow channels with said dissolution chamber; and
   (d) at least one evacuation port positioned within said body member for evacuating the air from a selected flow chamber prior to its being aligned with said dissolution chamber.

2. The dissolution cell of claim 1 further comprising retaining means positioned within each of said flow channels for retaining dissolvable solids.

3. The dissolution cell of claim 2 further comprising filter means positioned within said output port region.

4. The dissolution cell of claim 3 wherein said central aperture and said insert member are of mating elongated cylindrical shapes and the selective moving of said insert is substantially a linear translational motion.

5. The dissolution cell of claim 3 wherein said central aperture and said insert member are of mating truncated right circular cylindrical shapes and the selective moving of said insert is substantially a rotary motion.

6. The dissolution cell of claim 4 or claim 5 further comprising agitation means positioned within said input port region.

7. The dissolution cell of claim 3 further comprising a plurality of sealing means distributed so as to provide a pair of sealing means surrounding each of said flow channels.

8. The dissolution cell of claim 7 wherein said sealing means are O-rings.

9. The dissolution cell of claim 8 further comprising agitation means positioned within said input port region.

* * * * *